(12) United States Patent
Vesto (10) Patent No.: US 9,052,809 B2
(45) Date of Patent: Jun. 9, 2015

(54) SYSTEMS AND METHODS FOR SITUATIONAL APPLICATION DEVELOPMENT AND DEPLOYMENT WITH PATIENT EVENT MONITORING

(75) Inventor: Guy Robert Vesto, Kildeer, IL (US)

(73) Assignee: General Electric Company, Schenectady, NY (US)

(*) Notice: Subject to any disclaimer, the term of this patent is extended or adjusted under 35 U.S.C. 154(b) by 818 days.

(21) Appl. No.: 12/788,059

(22) Filed: May 26, 2010

(65) Prior Publication Data

US 2011/0295616 A1    Dec. 1, 2011

(51) Int. Cl.
| | |
|---|---|
| G06Q 50/00 | (2012.01) |
| G06F 3/0486 | (2013.01) |
| G06F 9/44 | (2006.01) |
| G06Q 10/06 | (2012.01) |
| G06Q 50/22 | (2012.01) |
| G06Q 50/24 | (2012.01) |
| G06F 19/00 | (2011.01) |

(52) U.S. Cl.
CPC ............. *G06F 3/0486* (2013.01); *G06F 8/34* (2013.01); *G06Q 10/06* (2013.01); *G06Q 50/22* (2013.01); *G06Q 50/24* (2013.01); *G06F 19/325* (2013.01)

(58) Field of Classification Search
CPC .... G06Q 50/22; G06Q 50/24; G06F 19/3418; G06F 19/322; G06F 19/327; A61B 5/0022
See application file for complete search history.

(56) References Cited

U.S. PATENT DOCUMENTS

| | | | |
|---|---|---|---|
| 6,092,102 A | 7/2000 | Wagner | |
| 6,604,093 B1 | 8/2003 | Etzion et al. | |
| 7,131,037 B1 | 10/2006 | LeFaive et al. | |
| 7,275,250 B1 | 9/2007 | Novik et al. | |
| 2005/0055246 A1* | 3/2005 | Simon | 705/2 |
| 2006/0205564 A1* | 9/2006 | Peterson | 482/8 |
| 2007/0168223 A1* | 7/2007 | Fors et al. | 705/2 |
| 2008/0288500 A1 | 11/2008 | Sapounas | |

(Continued)

FOREIGN PATENT DOCUMENTS

JP    2004348680    12/2004

OTHER PUBLICATIONS

Cherbakov et al., "SOA meets situational applications, Part 1: Changing computing in the enterprise," <http://www.ibm.com/developerworks/webservices/library/ws-soa-situational1/>, Aug. 23, 2007. (10 pages).

(Continued)

*Primary Examiner* — Michelle L Le (57) ABSTRACT

Systems and methods for clinical event processing with situational awareness to dynamically facilitate a clinician's workflow are provided. An example clinical event processing and situational awareness system includes a clinical event processor including a clinical event processing engine and a routing engine to receive information regarding a clinical event from an event source and to process the information regarding the clinical event to determine a clinical situation based on the clinical event. The system also includes an event handler to enrich the processed information regarding the clinical event by adding a clinical context to the processed information from a data source. The system further includes a dispatcher to notify a user and launch an anticipated application for the user to facilitate a situational aware clinical workflow based on the enriched, processed information regarding the clinical event.

20 Claims, 9 Drawing Sheets

(56) References Cited

U.S. PATENT DOCUMENTS

2009/0239508 A1  9/2009  Waddell
2009/0240526 A1  9/2009  Vesto et al.

OTHER PUBLICATIONS

Eric S. Toner, "Creating Situational Awareness: A Systems Approach," <http://www.iom.edu/~/media/Files/Activity%20Files/PublicHealth/MedPrep/Jun-10-11-2009-Commissioned%20Papers/Jun-10-11-2009-Commissioned-Paper-Creating-Situational-Awareness-A-Systems-Approach.ashx>, Jun. 10, 2009; retrieved online May 26, 2010. (6 pages).

Hazlehurst et al., "MediClass: A System for Detecting and Classifying Encounter-based Clinical Events in Any Electronic Medical Record," <http://www.ncbi.nlm.nih.gov/pmc/articles/PMC1205600/>, accepted May 8, 2005. (22 pages).

Rebecca Werbel, "Hippocrates: New Jersey's Health System Situational Awareness Application," New Jersey Department of Health and Senior Services Division of Health Infrastructure Preparedness & Emergency Response, from proceedings of ESRI Health GIS Conference, Oct. 8-10, 2007. (19 pages).

* cited by examiner

SYSTEMS AND METHODS FOR SITUATIONAL APPLICATION DEVELOPMENT AND DEPLOYMENT WITH PATIENT EVENT MONITORING

BACKGROUND

Hospitals and clinicians today are facing pressure to deliver high quality patient care, prevent adverse events/errors, and implement clinical best practices while reducing the cost of healthcare delivery. Furthermore, hospitals can face dramatic variation in clinical demand and are increasingly likely to be declined reimbursement when patient care falls short. Hospitals that operate at or over capacity may experience heightened rates of safety events. Current support is provided based on anticipated, static events, and do not account for chaos and unpredictability associated with many medical events.

BRIEF SUMMARY

Certain embodiments of the present invention provide systems and methods for clinical event processing with situational awareness to dynamically facilitate a clinician's workflow.

Certain examples provide a computer-implemented method for deploying clinical applications with situational awareness. The method includes receiving information regarding a clinical event from one or more event sources; processing, using a processor, the information regarding the clinical event to determine a clinical situation based on the clinical event; adding, using the processor, a clinical context to enrich the information regarding the clinical event; and providing a clinical application to a user in anticipation of a workflow involving the clinical situation.

Certain examples provide a clinical event processing and situational awareness system. The system includes a clinical event processor including a clinical event processing engine and a routing engine to receive information regarding a clinical event from one or more event sources and to process the information regarding the clinical event to determine a clinical situation based on the clinical event. The system also includes an event handler to enrich the processed information regarding the clinical event by adding a clinical context to the processed information from a data source. The system further includes a dispatcher to notify a user and enable launch of an anticipated application for the user to facilitate a situational aware clinical workflow based on the enriched, processed information regarding the clinical event.

Certain examples provide a tangible computer-readable storage medium having a set of instructions stored thereon which, when executed, instruct a processor to implement a clinical event processing and situational awareness system. The system includes a clinical event processor including a clinical event processing engine and a routing engine to receive information regarding a clinical event from one or more event sources and to process the information regarding the clinical event to determine a clinical situation based on the clinical event. The system also includes an event handler to enrich the processed information regarding the clinical event by adding a clinical context to the processed information from a data source. The system further includes a dispatcher to notify a user and launch an anticipated application for the user to facilitate a situational aware clinical workflow based on the enriched, processed information regarding the clinical event.

The foregoing summary, as well as the following detailed description of certain embodiments of the present invention, will be better understood when read in conjunction with the appended drawings. For the purpose of illustrating the invention, certain embodiments are shown in the drawings. It should be understood, however, that the present invention is not limited to the arrangements and instrumentality shown in the attached drawings.

DETAILED DESCRIPTION OF CERTAIN EMBODIMENTS

Although the following discloses example methods, systems, articles of manufacture, and apparatus including, among other components, software executed on hardware, it should be noted that such methods and apparatus are merely illustrative and should not be considered as limiting. For example, it is contemplated that any or all of these hardware and software components could be embodied exclusively in hardware, exclusively in software, exclusively in firmware, or in any combination of hardware, software, and/or firmware. Accordingly, while the following describes example methods, systems, articles of manufacture, and apparatus, the examples provided are not the only way to implement such methods, systems, articles of manufacture, and apparatus.

When any of the appended claims are read to cover a purely software and/or firmware implementation, at least one of the elements in an at least one example is hereby expressly defined to include a tangible medium such as a memory, DVD, CD, etc. storing the software and/or firmware.

Certain examples provide a software development and deployment platform that enables development, usage, and support of "situational healthcare applications" that have situation awareness. Such applications help enable healthcare providers to respond quickly to events by providing access to the right information and right tools at the right time. Situational healthcare applications are developed quickly by users that are closest to the healthcare delivery organizations and are easy to use, focused on specific business problems.

Hospitals and clinicians today are facing enormous pressures to deliver high quality patient care, prevent adverse events/errors, and implement clinical best practices while reducing the cost of healthcare delivery. Furthermore, hospitals can face dramatic variation in clinical demand and increasingly face the likelihood of being turned down for reimbursement when patient care falls short. It has been proven that hospitals that operate at or over capacity may experience heightened rates of safety events and might consider re-engineering the structures of care to respond better during periods of high stress.

Healthcare information technology (IT) systems can help hospitals overcome many of these challenges. To this end, clinicians need clinical data in real-time so that they can respond to an event as quickly as possible to prevent or reduce any adverse impact. Real-time alerts and escalations in hospitals can lead to forecasting, detecting and correcting adverse development in patient status. The alerts can impact outcomes such as lengths of stay, criticality of event, survival and death. However, the clinicians' time to interact with IT systems is limited especially under periods of stress. They need access to the right information and the right tool at the right time.

Many state-of-the-art Clinical Information Systems today can provide the alerting, clinical decision support and best practice guidance, which can result in better outcome and improved healthcare delivery. However, more often these applications are built where events are anticipated and planned for while healthcare delivery can at times be chaotic. Certain examples described herein provide an advantage over traditional clinical information system by providing a "situational application platform" specifically designed to handle uncertainty and change. In busy healthcare delivery organizations, decisions are made as closely as possible to the time when actions must be taken. Doctors often must make decisions on the spot consistent with the patients needs and they have limited time to interact with computers. Responses have to be determined on the fly.

Situational awareness (SA) involves being aware of what is happening around you to understand how information, events, and your own actions will impact your goals and objectives, both now and in the near future. Certain examples attempt to anticipate a clinician's responses to various events (via situational awareness logic) and provide a simplified (e.g., "one click") access to the right workflow applications for the given situations. This reduces the doctor's interaction time with computers.

Certain examples can be provided as a standalone product or can be bundled with other clinical information system(s) and/or medical device(s). Certain examples provide an adaptive workflow enhancement tool. Certain examples provide synergies between medical device and healthcare IT products. The situational platform enables healthcare providers to create innovative solutions themselves, promote the solutions, and share the solutions with others. The extensible development platform can be a catalyst for partnerships and can provide an ecosystem for customer collaboration, for example.

Situational awareness can be employed for a variety of purposes in healthcare. For example, situational awareness can be used in disease detection and surveillance, Health Alert Networks (e.g., the Center for Disease Control (CDC) and state health departments sending alerts to clinicians), news and Web trawling (e.g., mining global news for disease reports), bed tracking, patient tracking, incident command systems, electronic health records with alerting and decision support, etc.

Certain examples provide situational awareness along with a situational awareness platform narrowed to the healthcare domain to provide workflows for clinicians in anticipation of a response to a given event.

Healthcare SAs can help provide quick solutions for unanticipated and unplanned events where traditional applications have been built for which events and responses are planned and anticipated. In certain examples, healthcare SAs utilize "mashups". A "mashup" is built by taking multiple disparate data sources and creating a new data source. For example, mashups allow users to take maps, charts, videos, and data and mash them together into a visually interesting experience for the user.

In certain examples, a focus is on clinical event processing and situation detection rather than data aggregation from Internet sources. Additionally, certain examples provide "Situation Awareness" which relates to a perception of an environment critical to decision-makers in complex, dynamic areas. Furthermore, certain examples leverage "Complex Event Processing" (CEP). CEP is a technology used to detect complex patterns of many events, event correlation and abstraction, event hierarchies, and relationships between events such as causality, membership, and timing, and event-driven processes.

In certain examples, events from multiple event sources are processed (see e.g., FIGS. 4-7 and other examples described below). Certain examples provide post-processing of events/alerts that can be generated by clinical decision support (CDS) systems and/or other sources and can correlate multiple events and series of complex events. Situational awareness logic provides an ability for physicians to tailor alert notification to their specific workflows to avoid "alert fatigue" whereby the physician starts tuning out alerts because of their constant volume, for example.

Figure 1:
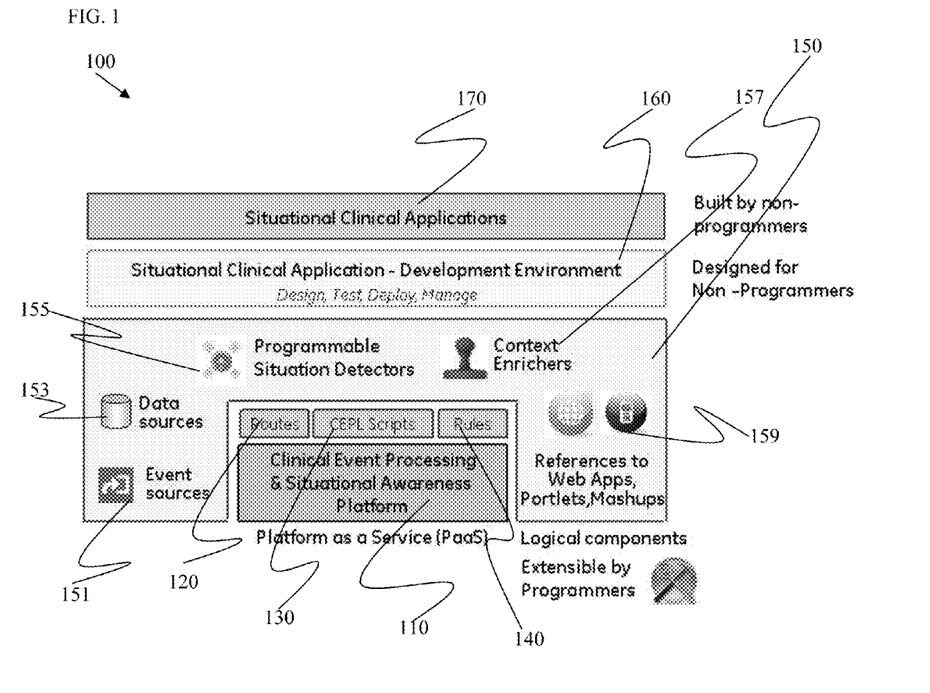
FIG. 1 illustrates a high-level overview of an example situational awareness platform is shown.

Turning to FIG. 1, a high-level overview of an example situational awareness platform 100 is shown. The platform 100 includes a clinical event processing and situational awareness infrastructure platform 110, event routes 120, scripts 130, rules 140, logical components 150, a situational clinical application integrated development environment 160, and situational clinical applications 170.

The runtime Clinical Event Processing and Situational Awareness infrastructure platform 110 executes Clinical Event Processing Language (CEPL) scripts 130, routes events 120, and evaluates situational awareness rules 140. The layer surrounding this infrastructure includes logical components 150. Logical components 150 include abstract building blocks that are used by non-programmers to "wire" together situational applications using the Integrated Development Environment 160. Logical components 150 in the layer surrounding the infrastructure 110 include event sources 151, data sources 153, programmable situation detectors 155, context enrichers 157, and references 159 to external content such as web applications, portlets, and mashups.

For example, event sources 151 include various event sources (e.g., patient monitors, hospital information systems, document registries, order systems, schedulers, etc.) that can trigger issuance of alerts and evaluation of complex event series. Data sources 153 include web services to electronic health records, clinical data repositories, electronic health records, virtual medical records, etc. Programmable situation detectors 155 include reusable complex event processing scripts for detecting combination of events or event patterns and for further querying data sources and evaluating responses. Context enrichers 157 include components for adding additional contextual information to event messages. References 159 include references to web applications, mobile apps and mashups. The logical components layer 150 also includes one or more application programming interfaces (APIs), which enable programmers and partners to add additional components and extensions.

Figure 2:
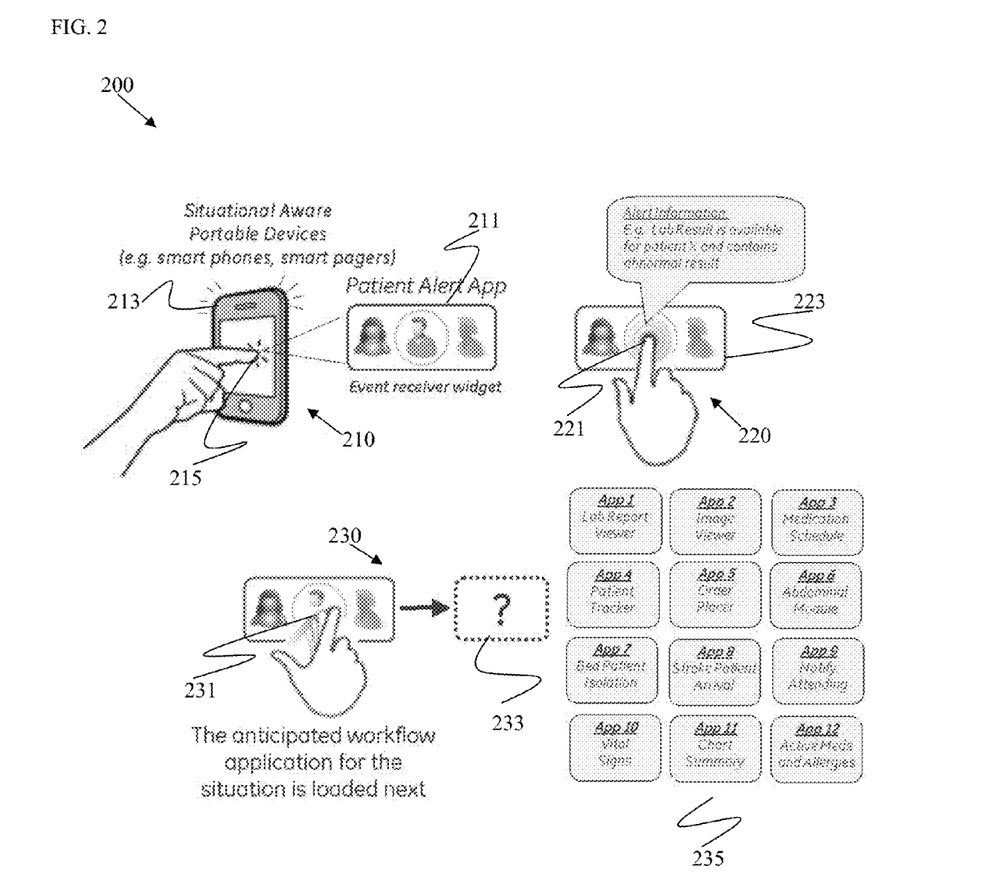
FIG. 2 depicts an example situational aware workflow facilitated using a smart phone or other mobile device.

The Situational Clinical Application Integrated Development Environment 160 enables non-programmers to implement healthcare specific situational applications 170, which also have some situation awareness. An example of such an application is shown in FIG. 2.

In certain examples, a mobile device, such as a smart phone (e.g., a BlackBerry™ iPhone™, etc.) or a tablet-based or other small form factor computer (e.g., an iPad™) can be enabled with situation awareness. As shown, for example, in FIG. 2, a situational aware workflow 200 is facilitated using a smart phone mobile device. At 210, a Patient Alert application 211 deployed on a smart phone 213 notifies a doctor, who touches the display 215 to view the alert message. To respond to the event, at 220, the doctor makes a simple touch screen gesture or click on an item 211 on the screen 213, for example. At 230, based on item 231 selection by the user, the smart phone knows which application 233 from a group of available applications 235 to load next to allow the doctor to respond to the event as quickly as possible. As shown in this example, there are several different "workflow" applications 235, which the doctor might want to use. However, because situation awareness is enabled, the most desirable application 233 is loaded.

Figure 3:
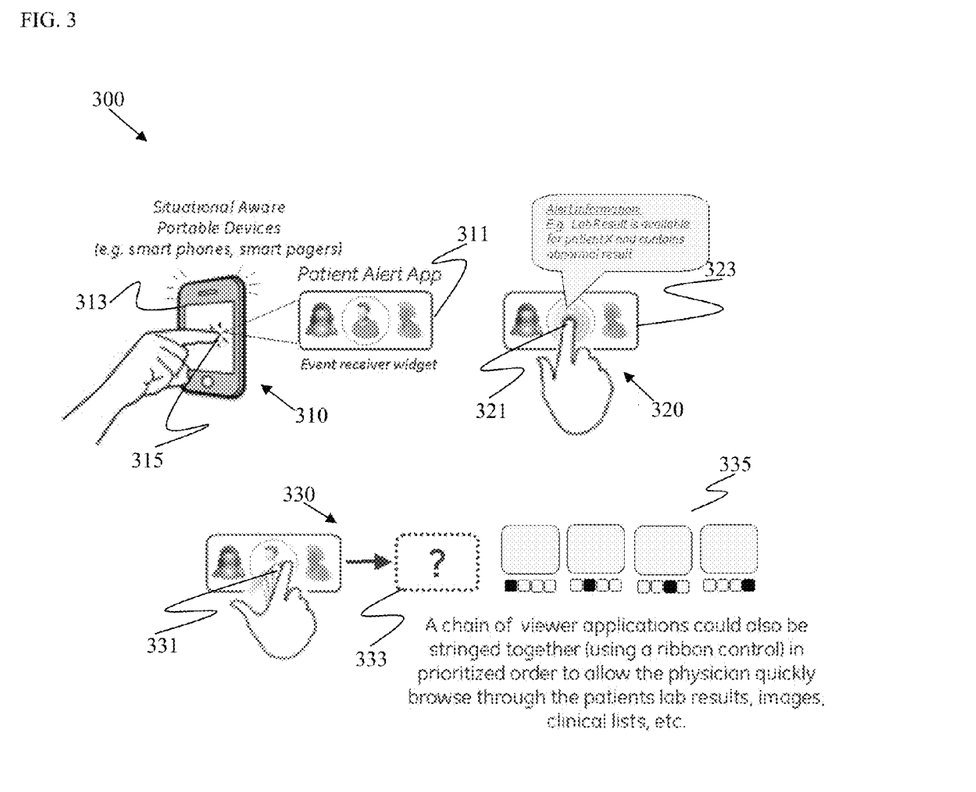
FIG. 3 depicts an example situational aware workflow facilitated using a smart phone or other mobile device.

A variation of this scenario is shown in FIG. 3. In the example workflow 300, a doctor can browse through a patient's medical information in a prioritized order that fits a particular situation and patient status or condition. Prioritization can be facilitated using situation awareness. As shown, for example, in FIG. 3, a situational aware workflow 300 is facilitated using a smart phone mobile device. At 310, a patient alert application 311 deployed on a smart phone 313 notifies a doctor, who touches the display 315 to view the alert message. To respond to the event, at 320, the doctor makes a simple touch screen gesture or click on an item 311 on the screen 313, for example. At 330, based on item 331 (e.g., patient) selection by the user, the smart phone loads an appropriate application 333 providing access to health information for the patient that is present to the doctor via the smart phone in a prioritized order. The order allows the clinician to quickly browse through the patient's information, such as lab results, images, clinical lists, etc. In some examples, a chain of viewer applications 335 can be provided together (e.g., using a ribbon control) in prioritized order to allow the clinician to quickly browse through patient lab results, images, clinical lists, etc.

The following are some other examples of healthcare specific situational applications, which can be built using systems and methods disclosed herein.

One example use case is laboratory test results notification. An opportunity for workflow improvement within a hospital involves coordinating results from the laboratory with a patient's antibiotics and isolation status. If an organism is identified that requires a patient to be isolated, the situationally aware application automatically begins a process that simultaneously communicates to nursing, admissions, the physician, and the housekeeping staff so the patient is quickly moved to an isolation room, limiting others' exposure. Furthermore, abnormal laboratory test results for a patient with abdominal pain can allow the clinician, through a single click (or gesture), to retrieve relevant information such as the patient's white blood cell count, serum amylase, and images from an abdominal ultrasound. The situationally aware clinical application can also assemble the most likely orders the clinician might chose including those that comply with adopted guidelines.

Another example use case is a situation in which a patient is crashing. A situationally aware event processing application can be built which monitors alerts from bedside medical devices such as patient monitors, pulse oximetry, ventilators, etc. The alerts can be provided in the form of heart rate changes, low SpO2, Tachycardia (heart beating too fast), Bradycardia (heart beating too slow), respiration rates changes, electrocardiogram (ECG) information, ventilator disconnects, etc. Complex event processing logic can evaluate series of these events over time and rapidly determine whether the patient is crashing or is about to crash. An attending physician and nursing staff can then be alerted and provided with information about the patient current location and critical care information. This would be an additional level of alerting on top of what is already provided by the devices themselves.

Another example use case is stroke patient coordination. In stroke patient coordination, it is beneficial to coordinate care in the emergency department (ED) with urgent studies in radiology. When a patient comes to the ED with a possible stroke, there is a very short time span in which treatment can effectively reverse its effects. This requires coordination between the ED personnel who must evaluate the patient, and the radiology department where a procedure is needed to rule out a ruptured blood vessel. The situationally aware application alerts ED personnel to the risk of stroke so that the patient is assessed promptly and also alerts radiology personnel so they can conduct and interpret a computed tomography (CT) scan immediately. The SA clinical application can also help to reschedule other radiology patients that may need to be delayed to accommodate the emergency and can coordinate clot-busting medication for immediate administration to the ED patient.

Another example use case is escalations for overdue orders. A situationally aware clinical application can automatically escalate clinical orders to a next clinician on staff if the order is not carried out within an assigned timeframe, so that patients receive care when they need it. The system recognizes a patient's diagnosis and pre-populates order sets based on that information, presenting the clinician with the most logical choices and making it easier to make the right decision.

Figure 4:
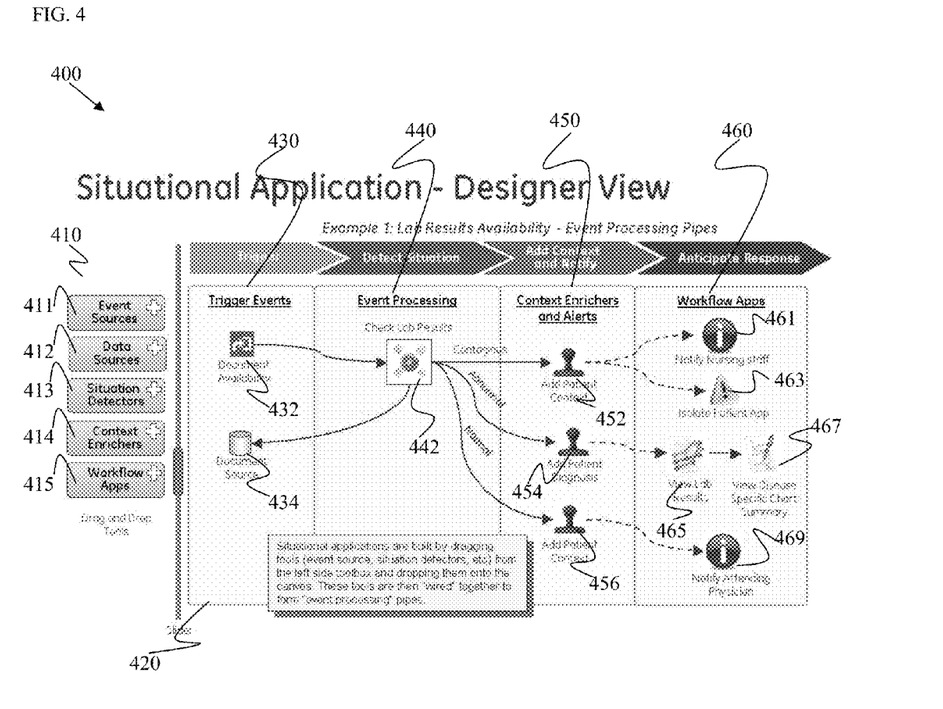
FIG. 4 depicts an example situational clinical application integrated development environment.

FIG. 4 depicts an example Situational Clinical Application Integrated Development Environment (IDE) 400. The IDE 400 is intended for non-programmers to quickly assemble healthcare specific situational applications. The IDE 400 is used to create event-processing flows, which wire together clinical event sources, detect situations, and link events to anticipated workflow applications. This is done through drag and drop configuration without requiring programming.

The IDE 400 includes a toolbar 410 that can be expanded to view individual tools 411-415 and a canvas 420 including a plurality of columns for trigger events 430, rules for detecting situations 440, context enrichers and alerts 450, and rules for an anticipated response 460. Using drag and drop operations, components can be wired or linked together to form processing flows and situational applications. Situational applications are generated by dragging tools (e.g., event sources 411, data sources 412, situation detectors 413, context enrichers 414, workflow applications 415, etc.) from the toolbox 410 and dropping them onto the canvas 420. These tools are then "wired" or linked together to form "event processing" pipes.

The example shown on FIG. 4 illustrates how a laboratory test results notification use case, described above, can be implemented. Trigger events 430 include a document availability event source 432 that receives notification events from a notification broker connected to a document source 434 (e.g., a Cross-Enterprise Document Sharing (XDS)-based document registry) whenever lab results are registered. Event processing 440 includes a situation detector for lab testing 442 that invokes the XDS-based document registry 434 to evaluate the content of the lab results. The lab results detector 442 can be implemented as a rule-based message router, for example. The router can be a dynamic router that can self-configure based on special configuration messages from participating destinations, for example. An alert event message is generated and routed to respective event handlers depending upon the result, such as contagious disease 444, abnormal test result 446, and normal test result 448. As part of context enrichment 450, the event message 44, 446, 448 is further enriched with patient context 452, 456 and/or diagnosis information 454 depending upon the detected situation.

An anticipated workflow application 460 uniform resource indicator (URI) (e.g., a link) is added to the event message before it is sent to subscribing users. For example, a contagious disease alert 444 with patient context 452 can be routed to an application 461 to notify nursing staff of the contagious disease patient and/or an isolate patient application 463 to isolate the contagious patient from other patients and personnel. As another example, an abnormal test result alert 446 with a patient diagnosis 454 can be routed to a view lab results application 465 and then to a view disease specific chart summary 457. As another example, a normal test result alert 448 including patient context 456 is sent to a notifying attending physician application 469.

Figure 5:
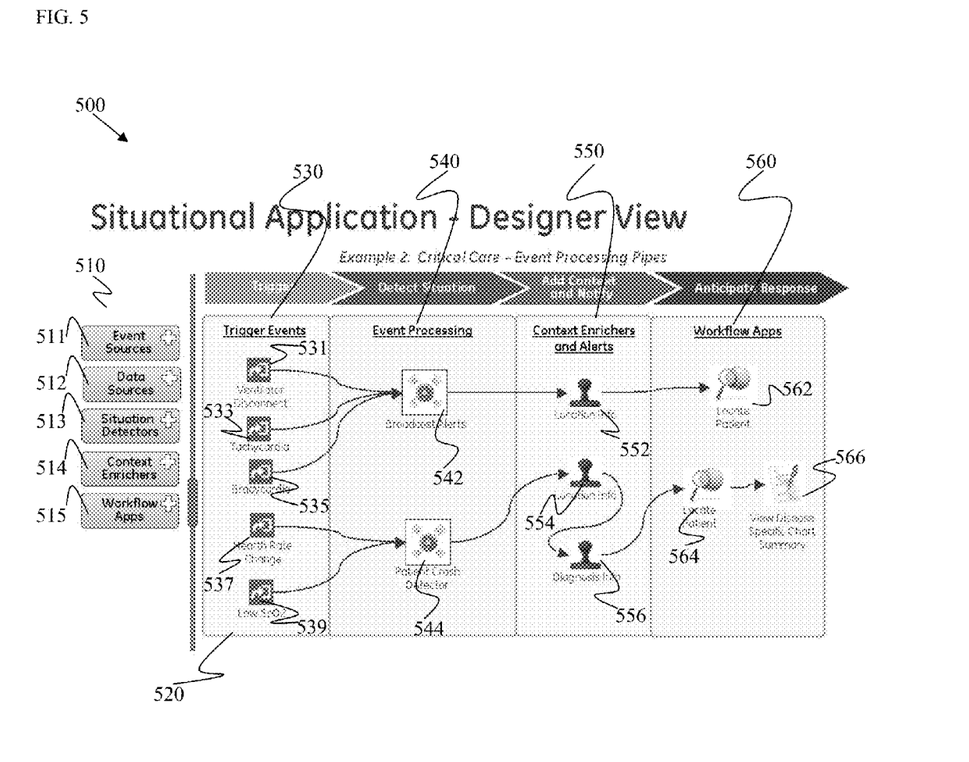
FIG. 5 depicts an example situational clinical application integrated development environment.
Figure 6:
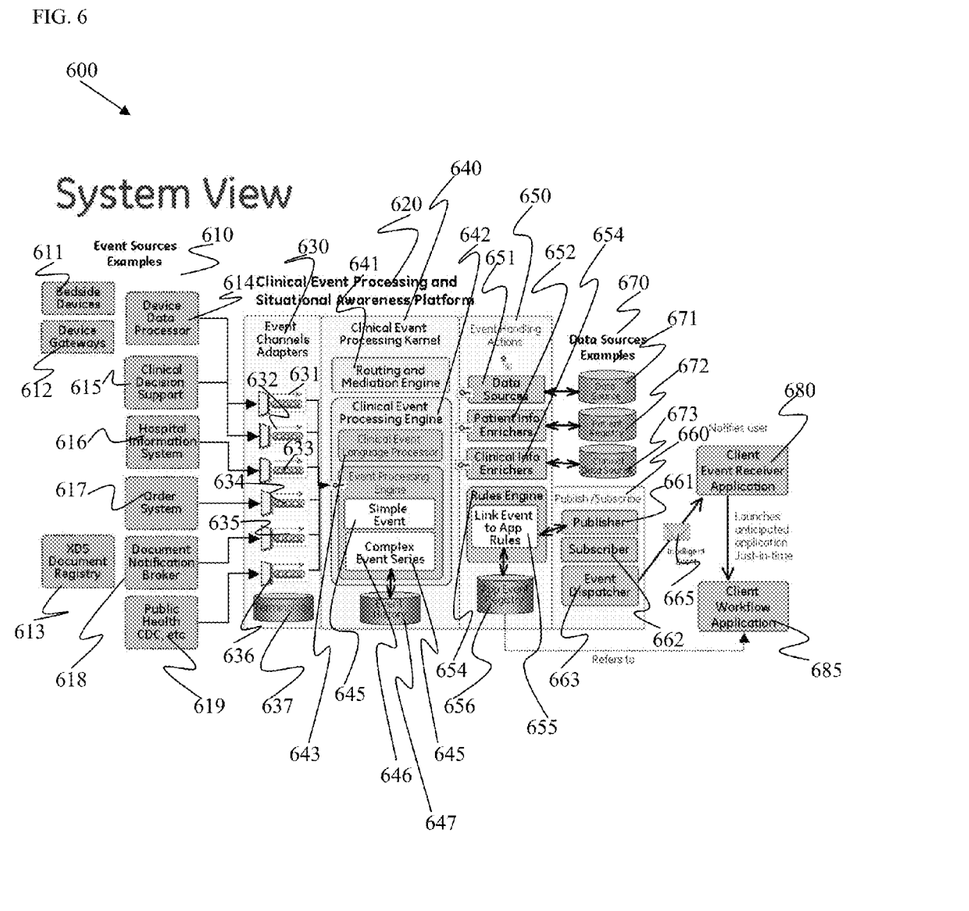
FIG. 6 illustrates an example clinical event processing system with situational awareness.

FIG. 5 shows an example Situational Clinical Application Integrated Development Environment (IDE) 500. The example shown on FIG. 5 illustrates how critical care event alerting, described above, can be implemented. The example IDE 500 can be connected to a medical device processor, such as the medical device processor described in US Patent Application Publication No. 20090240526, "Systems and Methods for a Medical Device Processor," which is herein incorporated by reference in its entirety. In some examples, the IDE 500 can be connected to multiple event sources, as shown in FIG. 6, including a clinical decision support engine, a hospital information system, a clinical data repository, an order system, a documentation notification broker, etc., in addition to a medical device data processor.

The IDE 500 includes a toolbar 510 that can be expanded to view individual tools 511-515 and a canvas 520 including a plurality of columns for trigger events 530, situation detectors 540, context enrichers and alerts 550, and anticipated response workflow applications 560. Using drag and drop operations, components can be wired or linked together to form processing flows and situational applications. Situational applications are generated by dragging tools (e.g., event sources 511, data sources 512, situation detectors 513, context enrichers 514, workflow applications 515, etc.) from the toolbox 510 and dropping them onto the canvas 520. These tools are then "wired" or linked together to form "event processing" pipes.

Trigger events 530 include ventilator disconnect 531, Tachycardia 533, Bradycardia 535, heart rate change 537, and low SpO2 539. The trigger event sources 530 are connected to situation detectors 540 including broadcast alerts 542 and patient crash detector 544. The detectors 542, 544 provide instructions for a complex event processing engine 540, which detects patterns in the incoming event streams 531, 533, 535, 537, 539. For example, ventilator disconnect 531, Tachycardia 533, and Bradycardia 535 events trigger broadcast notifications 542 to nursing staff and clinicians. The event message from broadcast alert 542 is enriched with the patient's location, bed number, etc. 552 and linked to a patient locator application 562. The heart rate change 537 and low SpO2 539 events are evaluated using the patient crash detector 544 to determine if the patient is crashing or about to crash. Crash detection alerts are enriched with patient location information 554 and diagnosis information 556 and linked to a patient locator application 564 along with a disease specific chart summary view 566.

In certain examples, once a clinical situation application has been created using the IDE 400, 500, the application can be published (shared with others), modified, and copied.

FIG. 6 illustrates an example clinical event processing system with situational awareness 600. The system 600 includes a plurality of event sources 610, such as bedside devices 611, device gateways 612, XDS document registry 613, a device data processor 614, clinical decision support 615, a hospital information system 616, an order system 617, a document notification broker 618, and a public health source 619 (Center for Disease Control, etc.). The system also includes a clinical event processing and situational awareness platform 620, which receives event information from the plurality of event sources 610. The platform 620 includes a plurality of event channel adapters 630, a clinical event processing kernel 640, an event handler 650, and a publish/subscribe engine 660. The event handler 650 exchanges information with one or more data sources 670. The platform 620 also communicates with a client event receiver application 680 and a client workflow application 685.

Event channel adapters 630 include a plurality of adapters 631-636 along with a terminology 637 to aid in understanding and conversion of event source 610 information for the platform 620. Events are adapted and routed to the clinical event processing kernel 640. The kernel 640 includes a routing and mediation engine 641 and a clinical event processing engine 642. The clinical event processing engine receives adapted event information from the event channel adapters 630. The clinical event processing engine 642 includes a clinical event language processor 643 and an event processing engine 644. The event processing engine 644 includes a simple event processor 645 and a complex event series processor 646. The event processing engine 644 interacts with an event history 647, for example.

The clinical event processing kernel 640 provides information regarding the processed event(s) to the event handler 650. The event handler includes data sources 651, patient information enrichers 652, clinical information enrichers 653, and a rules engine 654. The rules engine 654 includes a link or connection to application rules 655, for example, and communicates with an application even registry 656, for example. The data source 651 in the event handler 650 can communicate with an external data source 671, for example. The patient information enricher 652 of the event handler 650 can communicate with an external patient registry 672, for example. The clinical information enricher 653 of the event handler 650 can communicate with an external clinical data source 673, for example.

The rules engine 654 of the clinical event processing engine 642 provides event handling information to the publish/subscribe engine 660. The publish/subscribe engine 660 includes a publisher 661, a subscriber 662, and an event dispatcher 663, for example. The event dispatcher transmits an "intelligent" event 665 to the client event receiver application 680. The client event receiver application 680 launches an anticipated application 685 just in time. The application event registry 656 can also communicate with the client workflow application 685.

The event sources 610 are examples of healthcare information technology (IT) applications that can be integrated with the system 600. These event source applications 611-619 are integrated via event channels and adapters 630 according to enterprise integration patterns. The terminology database 637 stores clinical concepts, such as device parameters and value sets, exposed by the IDE 400, 500 and the event sources 610 to facilitate integration.

The clinical event processing kernel 640 includes the complex event processing (CEP) engine 646, such as an Esper™ CEP engine. The CEP engine 646 is adapted for the healthcare domain via the clinical event language processor 643, which is responsible for translating between a user-friendly domain specific language and the more generic Event Processing Language (EPL). The event history database 647 is used by the complex event processing engine 646 to reference historical events. The routing and mediation engine 641 enables the event processing flows to be "wired" together using the situational application IDE (discussed above).

Event handling action 650 components, such as the rules engine 654 and content enrichers 652, 653, leverage healthcare standards such as Integrating the Healthcare Enterprise (IHE) Patient Identifier Cross Referencing (PIX), Patient Demographics Query (PDQ), and/or Query for Existing Data (QED) profiles to integrate with clinical data sources and EHR systems. The application and event registry 656, utilized by the rules engine 654, is a registry of workflow applications mapped to events/alerts.

The content enricher 652, 653 uses information inside an incoming message (e.g., key fields) to retrieve data from an external source 670. After the content enricher 652, 653 retrieves the required data from the resource, the enricher 652, 653 appends the data to the message. The original information from the incoming message may be carried over into the resulting message or may no longer be needed, depending on the receiving application.

A publish/subscribe infrastructure 660 is connected to an event dispatcher 663 which transmits the event/alert messages to subscribing client applications (event receiver applications) 680 over a desired protocol (e.g., Web Services (WS) Notification, e-mail, Extensible Messaging and Presence Protocol (XMPP), etc.). As examples, the client application can be a smart-phone application, an instant messaging type application, an in-box, a clinical information system, etc.

In certain examples, a mobile device, such as an iPhone™, iPod™, iPad™, BlackBerry™, etc., can be used to allow a user to display and interact with clinical content stored on one or more clinical systems via the mobile device. A user can manipulate content, access different content, and collaborate with other users to analyze and report on exams and other medical content. In some examples, a change in device orientation and/or position results in a change in device mode and set of available tools without closing or losing the patient context and previous screen(s) of patient information. Images can be manipulated, annotated, highlighted, and measured via the device. Enterprise functionality and real-time collaboration are provided such that the user can collaborate on a document in real time with other users as well as access content from systems such as a radiology information system (RIS), picture archiving and communication system (PACS), hospital information system (HIS), electronic medical record (EMR), cardiovascular information system (CVIS), laboratory information system (LIS), etc., and make changes via the mobile device. The Situational Clinical Application IDE 400, 500 and clinical event processing and situational awareness system 600.

The mobile device can display and interact with medical content via a plurality of modes. Each mode includes different content and associated tools. Each of the plurality of modes is accessible based on a change in orientation and/or position of the device while maintaining a patient context across modes. The mobile device also includes medical content analysis capability for display, manipulation, and annotation of medical content and real-time sharing of the content for user collaboration using multi-touch control by the user. The mobile device communicates with one or more clinical systems to access and modify information from the one or more clinical systems in substantially real-time.

The mobile device can be used to facilitate user workflow. For example, the mobile device uses an accelerometer and/or global positioning sensor and/or other positional/motion indicator to allow a user to navigate through different screens of patient content and functionality. The mobile device removes the requirement of using a user interface control to select between different screens. For example, multi-touch capability is provided to manipulate and modify content. Using multi-touch, a user can draw shapes and annotate to generate measurements, highlight abnormal structure, and/or add textual comments to an image, for example. Via the mobile device, a user can input and/or manipulate without adding external input devices. The position and motion sensor (s) are used to manipulate the navigation direction in the colonoscopy and/or the navigation speed, for example.

In certain examples, the mobile device provides enhance resetability for the user. For example, the device can undo, erase, and/or reset end user changes to default setting by tracking a device's position and/or orientation and responding to changes to the position/orientation. The device can undo and restart without additional user interface control input. The device can adjust a threshold parameter through user feedback, for example (e.g., a current setting may be too sensitive to normal movement of the device when carried or held by a user).

Certain examples integrate enterprise functions into a mobile device. For example, functionality such as a directory, calendar, geographic location, phone services, text message, email, etc., can be provided via the mobile device. Clinical information from various sources such as PACS, HIS, RIS, EMR, CVIS, LIS, etc., can be provided via the mobile device. The mobile device interface can facilitate real-time collaboration with other end users. Information sharing and recording can be facilitated using multiple media services in real-time or substantially real-time, for example. The mobile device allows the user to focus on patient information and analysis while collaborating with one or more end users without switching or leaving the clinical context being reviewed, as well as exchanging medical data without losing the current state of the clinical context, for example. The mobile device provides a unified communication/collaboration point that can query and access information throughout different information systems, for example.

Certain examples facilitate user authentication via the mobile device. For example, the mobile device can authenticate a user's access to sensitive and/or private information. In certain embodiments, user authentication at the mobile device does not require the user to enter an identifier and password. Instead, the user is known, and the mobile device verifies if the current user is authorized for the particular content/application. Authentication is based on a unique identification number for the device, a connectivity parameter, and a PIN number for the user to enter, for example.

In some examples, a user is provided with an ability to share findings and a walk-through of the findings using a smartphone (e.g., BlackBerry™, iPhone™, etc.) or other handheld device such as an iPod™ or iPad™. Doctors can discuss the findings with the patient by replaying the reading, for example. In some examples, a user is provided with an ability to have a second opinion on the findings from a specialist and/or another radiologist without being in proximity to a workstation. The reading radiologist can contact a specialist for a second opinion and to provide feedback (e.g., commentaries and/or annotations) on the same procedures. The first physician can review and acknowledge or edit (e.g., a document review with tracking changes) the second radiologist's annotation.

Figure 7:
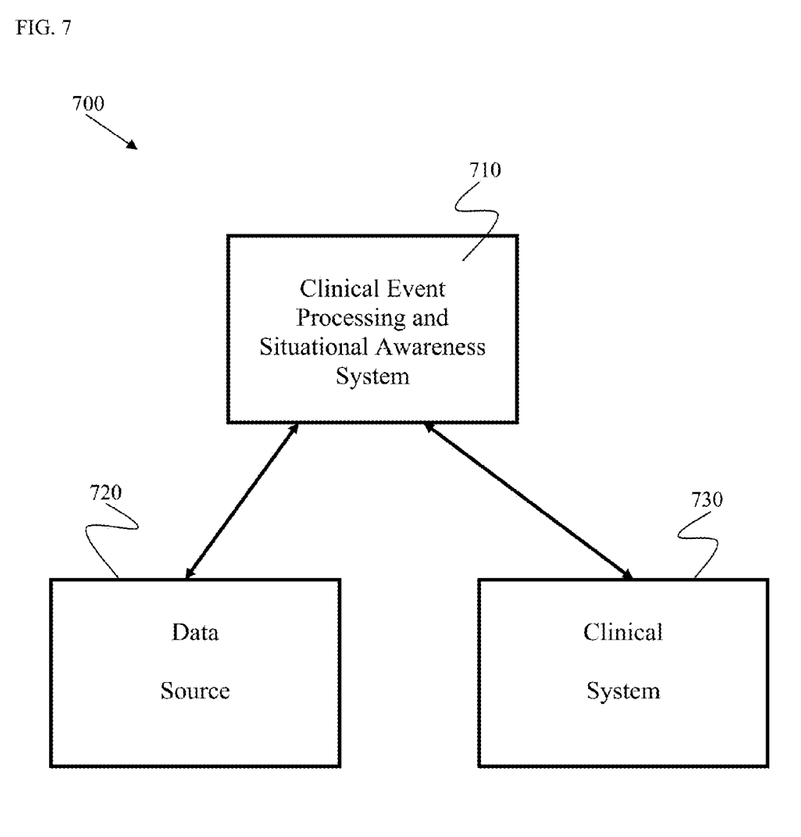
FIG. 7 depicts an example situational application platform for patient event monitoring.

FIG. 7 depicts an example situational application platform 700 for patient event monitoring. The platform 700 includes a clinical event processing and situational awareness system 710, a data source 720, and a clinical system 730. The clinical event processing and situational awareness system 710 can include one or more of the situational awareness platform 100; the IDE 400 and/or 500; and the clinical event processing and situational awareness platform 620 and its components, as described above with respect to FIG. 6. The system 710 exchanges information with the data source 720, which includes and/or communicates with one or more event and/or data sources such as logical components 150, toolkit sources 410 and/or 510, event source(s) 610, data source(s) 670, and the like. The system 710 facilitates development, deployment, and/or usage of one or more clinical applications having situational awareness based on patient event monitoring and stored clinical information. Applications are provided to the clinical system 730 to help facilitate a clinician's workflow. The clinical system 730 can include and/or communicate with a clinical information system (e.g., RIS, PACS, CVIS, LIS, HIS, EMR, etc.), a clinical imaging system (e.g., an x-ray system, an ultrasound scanner, a magnetic resonance imaging system, a computed tomography system, a digital radiography system, a nuclear imaging system, etc.), a practice/enterprise management system (e.g., a scheduling, billing, and/or other management system), and the like. In certain examples, the clinical system 730 can include and/or communicate with a user device, such as a computer, laptop, mobile phone (e.g., a BlackBerry™, a Palm™, an iPhone™, an iPad™, etc.) to facilitate user interaction with available information, situationally aware application(s), and associated workflow.

For example, the system 710 can facilitate a situationally aware workflow for a clinician via the clinical system 730, such as via a smart phone device (e.g., a BlackBerry™, iPhone™, etc.) or a tablet-based or other small form factor computer (e.g., an iPad™). Based on events and/or other information retrieved from the data source 710, the clinical event processing and situational awareness system 710 processes and deploys a patient alert application to the clinical system 730 to notify a clinician of a patient alert event. Based on a selection by the clinician via the clinical system 730, an application is loaded to allow the clinician to quickly respond to the event. The application is selected by the system 710 from several available applications based on the event(s) and/or other data that triggered the notification, situation detection processing the trigger(s), and context added to enrich the event trigger(s). In some examples, patient information and/or workflow application options can be provided to the clinician for browsing/review in a prioritized order based on the particular situation and patient status/condition. Prioritization can be facilitated using situation awareness. The prioritized order allows the clinician to quickly browse through the patient's information, such as lab results, images, clinical lists, etc. In some examples, a chain of clinical workflow applications can be provided together (e.g., using a ribbon control) in prioritized order to allow the clinician to quickly browse through patient lab results, images, clinical lists, etc., and available options for subsequent diagnosis and/or treatment.

Figure 8:
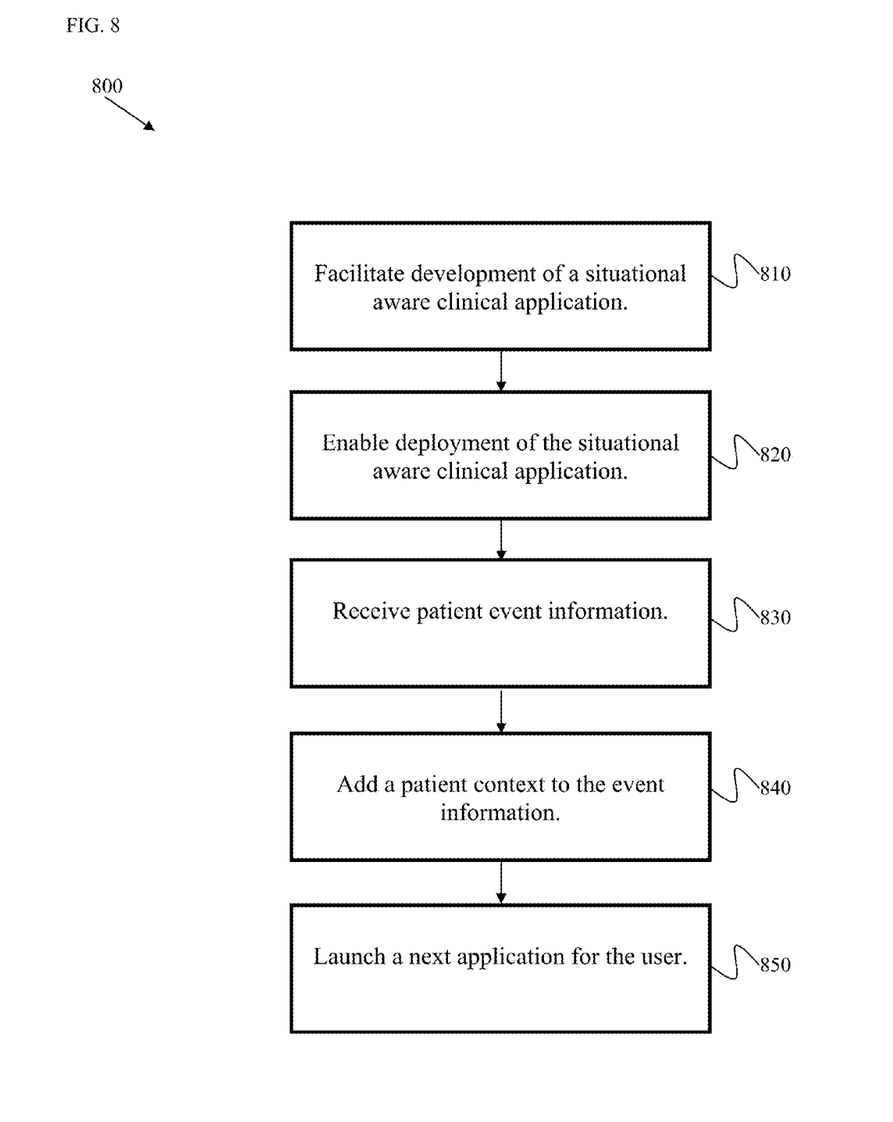
FIG. 8 illustrates a flow diagram for an example method for situational awareness clinical application development and deployment.

FIG. 8 illustrates a flow diagram for an example method 800 for situational awareness clinical application development and deployment. FIG. 8 depicts an example flow diagram representative of processes that may be implemented using, for example, computer readable instructions that may be used to facilitate reviewing of anatomical images and related clinical evidence. The example processes of FIG. 8 may be performed using a processor, a controller and/or any other suitable processing device. For example, the example processes of FIG. 8 may be implemented using coded instructions (e.g., computer readable instructions) stored on a tangible computer readable medium such as a flash memory, a read-only memory (ROM), and/or a random-access memory (RAM). As used herein, the term tangible computer readable medium is expressly defined to include any type of computer readable storage and to exclude propagating signals. Additionally or alternatively, the example processes of FIG. 8 may be implemented using coded instructions (e.g., computer readable instructions) stored on a non-transitory computer readable medium such as a flash memory, a read-only memory (ROM), a random-access memory (RAM), a cache, or any other storage media in which information is stored for any duration (e.g., for extended time periods, permanently, brief instances, for temporarily buffering, and/or for caching of the information). As used herein, the term non-transitory computer readable medium is expressly defined to include any type of computer readable medium and to exclude propagating signals.

Alternatively, some or all of the example processes of FIG. 8 may be implemented using any combination(s) of application specific integrated circuit(s) (ASIC(s)), programmable logic device(s) (PLD(s)), field programmable logic device(s) (FPLD(s)), discrete logic, hardware, firmware, etc. Also, some or all of the example processes of FIG. 8 may be implemented manually or as any combination(s) of any of the foregoing techniques, for example, any combination of firmware, software, discrete logic and/or hardware. Further, although the example processes of FIG. 8 are described with reference to the flow diagram of FIG. 8, other methods of implementing the processes of FIG. 8 may be employed. For example, the order of execution of the blocks may be changed, and/or some of the blocks described may be changed, eliminated, sub-divided, or combined. Additionally, any or all of the example processes of FIG. 8 may be performed sequentially and/or in parallel by, for example, separate processing threads, processors, devices, discrete logic, circuits, etc.

Referring to FIG. 8, at 810, a situational aware clinical application is developed. The application can be developed using a development environment, such as the integrated development environment 400 and/or 500 described above. At 820, the clinical SA application is deployed. For example, the developed application is made available to a clinical user via a personal computer and/or mobile device (e.g., a smart phone).

At 830, event information is received. For example, a sensor, monitor, and/or clinical system can trigger an alert regarding a patient condition (e.g., heart attack, stroke, blood pressure increase, lab results, upcoming exam, etc.) that is routed to the user via the clinical SA application. At 840, a patient context is added to the event information. For example, patient medical history information can be added to the current patient condition information. Patient location information can also be added to the event information, for example. By adding additional context around the event, a more accurate and/or more appropriate determination can be made dynamically regarding a next action in response to the event.

At 850, a next application is launched for the user. For example, based on the event and added context, a determination is made on-the-fly to launch a next application to facilitate the user's workflow with respect to the patient. The application can be launched in conjunction with an EMR, an imaging system, a clinical information system, etc., to facilitate the clinical workflow.

As described herein, the method 800 can be implemented using the mobile device in one or more combinations of hardware, software, and/or firmware, for example. The method 800 can operate with the mobile device in conjunction with one or more external systems (e.g., data sources, healthcare information systems (RIS, PACS, CVIS, HIS, EMR, etc.), archives, imaging modalities, etc.). One or more components of the method 800 can be reordered, eliminated, and/or repeated based on a particular implementation, for example.

Figure 9:
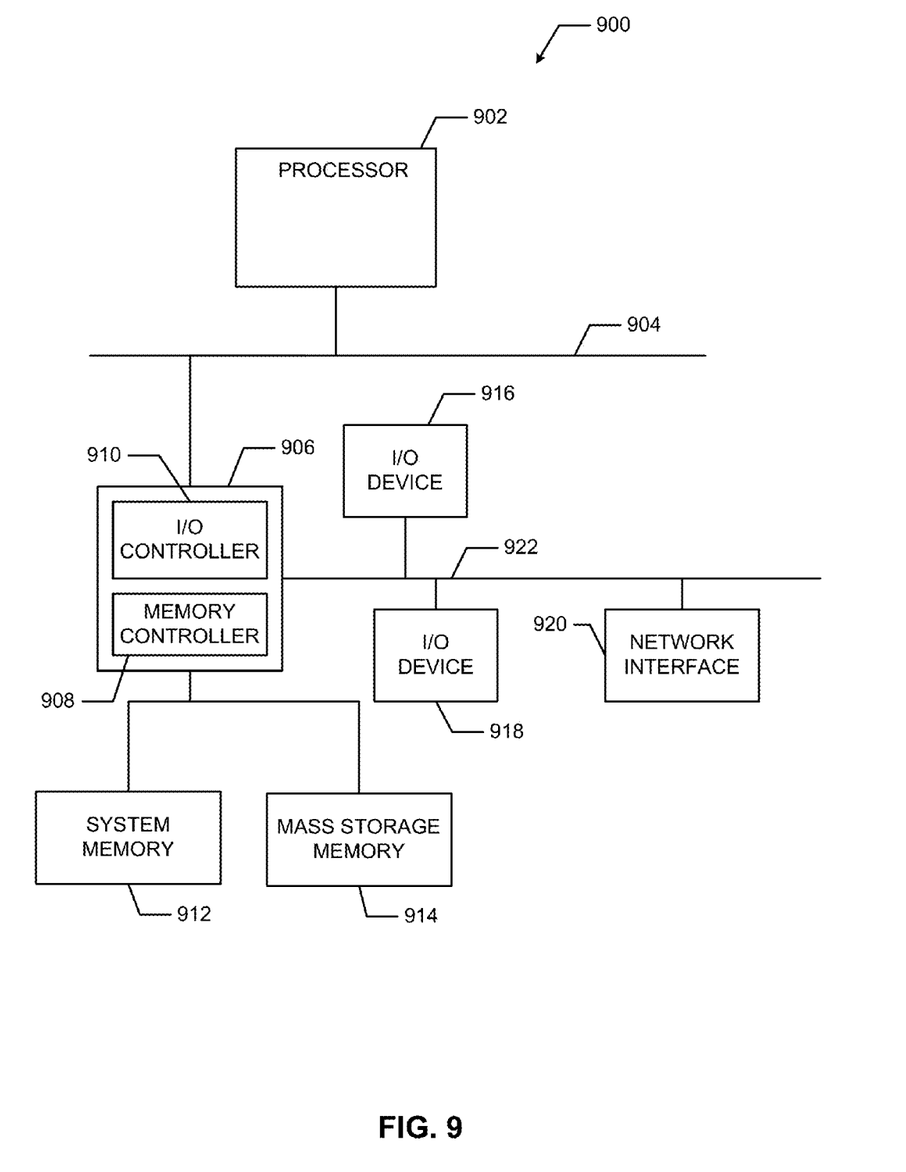
FIG. 9 is a block diagram of an example processor system that can be used to implement the apparatus and methods described herein.

FIG. 9 is a block diagram of an example processor system 910 that can be used to implement the apparatus and methods described herein. As shown in FIG. 9, the processor system 910 includes a processor 912 that is coupled to an interconnection bus 914. The processor 912 may be any suitable processor, processing unit or microprocessor. Although not shown in FIG. 9, the system 910 can be a multi-processor system and, thus, can include one or more additional processors that are identical or similar to the processor 912 and that are communicatively coupled to the interconnection bus 914.

The processor 912 of FIG. 9 is coupled to a chipset 918, which includes a memory controller 920 and an input/output (I/O) controller 922. As is well known, a chipset typically provides I/O and memory management functions as well as a plurality of general purpose and/or special purpose registers, timers, etc. that are accessible or used by one or more processors coupled to the chipset 918. The memory controller 920 performs functions that enable the processor 912 (or processors if there are multiple processors) to access a system memory 924 and a mass storage memory 925.

The system memory 924 can include any desired type of volatile and/or nonvolatile memory such as, for example, static random access memory (SRAM), dynamic random access memory (DRAM), flash memory, read-only memory (ROM), etc. The mass storage memory 925 can include any desired type of mass storage device including hard disk drives, optical drives, tape storage devices, etc.

The I/O controller 922 performs functions that enable the processor 912 to communicate with peripheral input/output (I/O) devices 926 and 928 and a network interface 930 via an I/O bus 932. The I/O devices 926 and 928 can be any desired type of I/O device such as, for example, a keyboard, a video display or monitor, a mouse, etc. The network interface 930 may be, for example, an Ethernet device, an asynchronous transfer mode (ATM) device, an 802.11 device, a DSL modem, a cable modem, a cellular modem, etc. that enables the processor system 910 to communicate with another processor system.

While the memory controller 920 and the I/O controller 922 are depicted in FIG. 9 as separate blocks within the chipset 918, the functions performed by these blocks may be integrated within a single semiconductor circuit or may be implemented using two or more separate integrated circuits.

Thus, certain examples provide systems and methods for adaptive workflow enhancement. Certain examples provide a software development and deployment platform that enables development, usage, and support of "situational healthcare applications" that have situation awareness. Such applications help enable healthcare providers to respond quickly to events by providing access to the right information and right tools at the right time. Situational healthcare applications are developed quickly by users that are closest to the healthcare delivery organizations and are easy to use, focused on specific business problems.

Situational awareness application development, deployment, and support provides synergies between medical devices and healthcare IT products. The situational platform enables healthcare providers to create innovative solutions themselves, promote them and share them with others. The extensible development platform can serve as a catalyst for partnerships and provide an ecosystem for customer collaborations.

Certain embodiments contemplate methods, systems and computer program products on any machine-readable media to implement functionality described above. Certain embodiments may be implemented using an existing computer processor, or by a special purpose computer processor incorporated for this or another purpose or by a hardwired and/or firmware system, for example.

One or more of the components of the systems and/or steps of the methods described above may be implemented alone or in combination in hardware, firmware, and/or as a set of instructions in software, for example. Certain embodiments may be provided as a set of instructions residing on a computer-readable medium, such as a memory, hard disk, DVD, or CD, for execution on a general purpose computer or other processing device. Certain embodiments of the present invention may omit one or more of the method steps and/or perform the steps in a different order than the order listed. For example, some steps may not be performed in certain embodiments of the present invention. As a further example, certain steps may be performed in a different temporal order, including simultaneously, than listed above.

Certain embodiments include computer-readable media for carrying or having computer-executable instructions or data structures stored thereon. Such computer-readable media may be any available media that may be accessed by a general purpose or special purpose computer or other machine with a processor. By way of example, such computer-readable media may comprise RAM, ROM, PROM, EPROM, EEPROM, Flash, CD-ROM or other optical disk storage, magnetic disk storage or other magnetic storage devices, or any other medium which can be used to carry or store desired program code in the form of computer-executable instructions or data structures and which can be accessed by a general purpose or special purpose computer or other machine with a processor. Combinations of the above are also included within the scope of computer-readable media. Computer-executable instructions comprise, for example, instructions and data which cause a general purpose computer, special purpose computer, or special purpose processing machines to perform a certain function or group of functions.

Generally, computer-executable instructions include routines, programs, objects, components, data structures, etc., that perform particular tasks or implement particular abstract data types. Computer-executable instructions, associated data structures, and program modules represent examples of program code for executing steps of certain methods and systems disclosed herein. The particular sequence of such executable instructions or associated data structures represent examples of corresponding acts for implementing the functions described in such steps.

Embodiments of the present invention may be practiced in a networked environment using logical connections to one or more remote computers having processors. Logical connections may include a local area network (LAN) and a wide area network (WAN) that are presented here by way of example and not limitation. Such networking environments are commonplace in office-wide or enterprise-wide computer networks, intranets and the Internet and may use a wide variety of different communication protocols. Those skilled in the art will appreciate that such network computing environments will typically encompass many types of computer system configurations, including personal computers, hand-held devices, multi-processor systems, microprocessor-based or programmable consumer electronics, network PCs, minicomputers, mainframe computers, and the like. Embodiments of the invention may also be practiced in distributed computing environments where tasks are performed by local and remote processing devices that are linked (either by hardwired links, wireless links, or by a combination of hardwired or wireless links) through a communications network. In a distributed computing environment, program modules may be located in both local and remote memory storage devices.

An exemplary system for implementing the overall system or portions of embodiments of the invention might include a general purpose computing device in the form of a computer, including a processing unit, a system memory, and a system bus that couples various system components including the system memory to the processing unit. The system memory may include read only memory (ROM) and random access memory (RAM). The computer may also include a magnetic hard disk drive for reading from and writing to a magnetic hard disk, a magnetic disk drive for reading from or writing to a removable magnetic disk, and an optical disk drive for reading from or writing to a removable optical disk such as a CD ROM or other optical media. The drives and their associated computer-readable media provide nonvolatile storage of computer-executable instructions, data structures, program modules and other data for the computer.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

The invention claimed is:

1. A computer-implemented method for deploying clinical applications with situational awareness, the method comprising:

receiving information regarding a clinical event from an event source;

processing, using a processor, the information regarding the clinical event to determine a clinical situation based on the clinical event, the processing including single event processing of the clinical event and complex series event processing of the clinical event and an event history associated with the clinical event to determine the clinical situation;

adding, using the processor, a clinical context to establish an enriched information regarding the clinical event;

identifying, automatically using the processor, a next anticipated clinical application based on the enriched information regarding the clinical event and the determined clinical situation, the next anticipated clinical application automatically determined for use by a healthcare provider and automatically configured based on the enriched information regarding the clinical event and the determined clinical situation; and providing the next anticipated clinical application to the healthcare provider on a device associated with the healthcare provider in anticipation of a clinical workflow involving the clinical situation to treat a patient.

2. The method of claim 1, wherein the clinical event comprises a complex clinical event series.

3. The method of claim 2, wherein processing further includes processing the information regarding the clinical event to determine the clinical situation based on a combination of clinical events including the complex clinical event series.

4. The method of claim 1, wherein providing the next anticipated clinical application facilitates a situational aware workflow via a mobile device.

5. The method of claim 1, wherein providing the next anticipated clinical application further comprises providing one or more next anticipated clinical applications relevant to the clinical situation for browsing and selecting by the healthcare provider.

6. The method of claim 1, further comprising building a situational aware clinical application via a development environment having a graphical user interface, building comprising:

facilitating healthcare provider drag and drop of tools including one or more event sources, data sources, situations detectors, context enrichers, and clinical workflow applications onto the graphical user interface divided into trigger events, event processing, context enrichers, and workflow applications;

connecting the tools placed on the graphical user interface to form the situational aware clinical application; and deploying the situational aware clinical application for use.

7. A clinical event processing and situational awareness system for operation by a healthcare provider, the system comprising:

a clinical event processor including a clinical event processing engine and a routing engine to receive information regarding a clinical event from an event source and to process the information regarding the clinical event to determine a clinical situation based on the clinical event, the clinical event processor including a single event processor to process the clinical event and a complex event series processor to process the clinical event and an event history associated with the clinical event, an output of the single event processor and the complex event series processor to determine the clinical situation;

an event handler to create an enriched, processed information regarding the clinical event by adding a clinical context to the information from the event source; and a dispatcher to notify the healthcare provider and launch a next anticipated clinical application for the healthcare provider on a device associated with the healthcare provider to facilitate a situational aware clinical workflow based on the enriched, processed information regarding the clinical event, the next anticipated clinical application to be identified automatically for use by the healthcare provider based on the enriched, processed information regarding the clinical event and the determined clinical situation, the next anticipated application automatically to be configured based on the enriched, processed information regarding the clinical event and the determined clinical situation.

8. The system of claim 7, wherein the clinical event processing engine includes one or more programmable situation detectors to process the enriched, processed information regarding the clinical event to determine a clinical situation based on the clinical event.

9. The system of claim 7, further comprising a plurality of event channel adapters, each to adapt information from an event source to be processed by the clinical event processor.

10. The system of claim 7, wherein the event handler comprises a rules engine.

11. The system of claim 7, wherein the clinical context includes at least one of a patient context, a clinical location context, and a diagnosis context.

12. The system of claim 7, wherein the clinical event comprises a complex clinical event series.

13. The system of claim 12, wherein the clinical event processor is to process the information regarding the clinical event to determine the clinical situation based on a combination of clinical events including the complex clinical event series.

14. The system of claim 7, wherein the dispatcher is to provide the anticipated application to facilitate a situational aware clinical workflow via a smart phone.

15. The system of claim 7, wherein the dispatcher is to provide one or more clinical applications relevant to the clinical situation for browsing and selecting by the healthcare provider.

16. The system of claim 7, further comprising an integrated development environment to build a situational aware clinical application comprising:
a graphical user interface to:
facilitate healthcare provider drag and drop of tools including one or more event sources, data sources, situations detectors, context enrichers, and clinical workflow applications onto an interface area divided into trigger events, event processing, context enrichers, and workflow applications;
connect the tools placed on the interface to form the situational aware clinical application; and
deploy the situational aware clinical application for use.

17. A tangible, non-transitory computer-readable storage medium having a set of instructions stored thereon which, when executed, instruct a processor to implement a clinical event processing and situational awareness system, the system comprising:
a clinical event processor including a clinical event processing engine and a routing engine to receive information regarding a clinical event from an event source and to process the information regarding the clinical event to determine a clinical situation based on the clinical event, the clinical event processor including a single event processor to process the clinical event and a complex event series processor to process the clinical event and an event history associated with the clinical event, an output of the single event processor and the complex event series processor to determine the clinical situation;
an event handler to enrich the processed information regarding the clinical event by adding a clinical context to the processed information from a data source; and
a dispatcher to notify a healthcare provider and enable launch of a next anticipated clinical application for the healthcare provider on a device associated with the healthcare provider to facilitate a situational aware clinical workflow based on the enriched, processed information regarding the clinical event, the anticipated clinical application to be identified automatically for use by the healthcare provider based on the enriched, processed information regarding the clinical event and the determined clinical situation, the anticipated application automatically to be configured based on the enriched, processed information regarding the clinical event and the determined clinical situation.

18. The tangible computer-readable storage medium of claim 17, wherein the clinical event processing engine includes one or more programmable situation detectors to process the information regarding the clinical event to determine a clinical situation based on the clinical event.

19. The tangible computer-readable storage medium of claim 17, wherein the clinical context includes at least one of a patient context, a clinical location context, and a diagnosis context.

20. The tangible computer-readable storage medium of claim 17, wherein the system further comprises an integrated development environment to build a situational aware clinical application comprising:
a graphical user interface to:
facilitate healthcare provider drag and drop of tools including one or more event sources, data sources, situations detectors, context enrichers, and clinical workflow applications onto an interface area divided into trigger events, event processing, context enrichers, and workflow applications;
connect the tools placed on the interface to form the situational aware clinical application; and
deploy the situational aware clinical application for use.

* * * * *